US006225438B1

(12) United States Patent
Green

(10) Patent No.: US 6,225,438 B1
(45) Date of Patent: May 1, 2001

(54) MEDIUM CHAIN LENGTH PHA COPOLYMER AND PROCESS FOR PRODUCING SAME

(75) Inventor: Phillip Richard Green, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/495,441

(22) Filed: Jan. 31, 2000

(51) Int. Cl.$^7$ .............................. C08G 63/06; C12D 7/62
(52) U.S. Cl. ......................... 528/361; 435/41; 435/135; 435/136; 435/141; 435/146; 435/822; 435/828; 435/831; 435/832; 435/842; 435/872; 435/874; 525/437; 525/444
(58) Field of Search ............................. 528/361; 435/41, 435/135, 136, 141, 146, 822, 828, 831, 832, 842, 872, 874; 525/437, 444

(56) References Cited

U.S. PATENT DOCUMENTS

| 4,433,053 | 2/1984 | Hughes et al. | 435/141 |
|---|---|---|---|
| 4,477,654 | 10/1984 | Holmes et al. | 528/361 |
| 5,292,860 | * 3/1994 | Shiotani et al. | 528/361 |
| 5,364,778 | 11/1994 | Byrom | 435/135 |
| 5,871,980 | 2/1999 | Naylor et al. | 435/135 |

FOREIGN PATENT DOCUMENTS

| 0 052 459 | 10/1981 | (EP) . |
|---|---|---|
| 0 440 165 | 1/1991 | (EP) . |
| 6-145311 | 6/1993 | (JP) . |
| WO 96/25509 | 8/1996 | (WO) . |

OTHER PUBLICATIONS

B.H.A. Rehm, et al., "PHA Synthesis in Recombinant *Escherichia coli*: Precursors are Provided via Fatty Acid α–Oxidation", *Symposium on "Polymers Made, Modified and Degraded by Biological Systems"*, p. 19, Jun. 2–6, 1998.

D. Dennis, et al., "Formation of poly(3–hydroxybutyrate–co–3–hydroxyhexanoate) by PHA synthase from *Ralstonia eutropha*", *J. of Biotech.* vol. 64, (1998), pp. 177–186.

Y. Doi, et al., "Prodaction and Characterization of Unusual Copolyesters by *Alcaligenes eutrophus*", *Polymer Preprints*, vol. 29, No. 1, (1998) pp. 588–589.

Song, et al., "Polyesters Biosynthesis of *Alcaligenes eutrophus* H16 (ATCC 17699) from Various Mono–and Dicarboxylic Acids and Diols", *J. of Microbiology and Biotechnology*, vol. 3, No. 2, pp. 123–128.

G. Eggink, et al., "Oleic acid as a substrate for poly–3–hydroxyalkanoate formation in *Alcaligenes eutrophus* and *Pseudomonas putida*", *Industrial Crops and Products*, vol. 1, (1993) pp. 157–163.

G.W. Haywood,et al., "The importance of PHB–synthase substrate specificity in polyhydroxyalkanoate synthesis by *Alcaligenes eutrophus*", *FEMS Microbiology Letters*, vol. 57, (1989), pp. 1–6.

R.V. Antonio, et al., "Analysis of in vivo substrate specificity of the PHA synthase from *Ralstonia eutropha*: formation of novel copolyesters in recombinant *Escherichia coli*", *FEMS Microbiology Letters*, vol. 182, (2000), pp. 111–117.

Q. Qi, et al, "Metabolic routing towards polyhydroxyalkanoic acid synthesis in recombinant *Escherichia coli* (fadR): inhibition of fatty acid β–oxidation by acrylic acid", *FEMS Microbiology Letters*, vol. 167, (1998), pp. 89–94.

H.W. Ulmer, et al., "The Bacterial Synthesis of Functional Poly(β–Hydroxyalkanoates)", *Polymer Preparation*, Vo. 30, No. 2, (1989), pp. 402–403.

A.J. Anderson, et al., "Biosynthesis and composition of bacterial poly(hydroxyalkanoates)", *Int. J. Bio. Macromol.*, vol. 12, (1990), pp. 102–105.

T.G. Volova, et al., "Biosynthesis of Heteropolymeric Polyhydroxyalkanoates by Chemolithoautotrophic bacteria", *Microbiology*, vol. 67, No. 4, (1998), pp. 420–424.

Liebergesel, et al., "Formation of poly(3–hydroxyalkanoates) by phototrophic and chemolithotrophic bacteria", *Archives of Microbiology*, vol. 155, (1991), pp. 415–421.

* cited by examiner

*Primary Examiner*—Samuel A. Acquah
(74) *Attorney, Agent, or Firm*—Cynthia M. Bott; Karen F. Clark

(57) ABSTRACT

This invention relates to polymer production and in particular to a novel copolymer and a process for microbiologically producing the same. More specifically this invention provides for a poly-3-hydroxyalkanoate (PHA) that includes medium length 3-hydroxyacyl monomers and a process comprising culturing a microorganism with a medium chain fatty carbon source and a fatty acid oxidation inhibitor. This invention allows the use of microorganisms which normally incorporate only short chain fatty acids to produce PHAs containing short and medium chain 3-hydroxyacyl monomers. The purpose of this invention is to produce a more versatile PHA polymer which includes C6, C7 and/or C8 3-hydroxyacyl monomers.

18 Claims, No Drawings

MEDIUM CHAIN LENGTH PHA COPOLYMER AND PROCESS FOR PRODUCING SAME

TECHNICAL FIELD

This invention relates to polymer production and in particular to a novel copolymer and a process for microbiologically producing the same. More specifically this invention provides for poly-3-hydroxyalkanoates (PHAs) that include medium length 3-hydroxyacyl monomers and a process for producing the copolymer comprising culturing a microorganism with at least one medium chain fatty carbon source and a fatty acid oxidation inhibitor. This invention allows the use of native microorganisms which normally incorporate only short chain fatty acids to produce PHAs containing short and medium chain 3-hydroxyacyl monomers. This invention provides a more versatile PHA polymer which includes 3-hydroxyheptanoate (C7) or 3-hydroxyoctanoate (C8) monomers.

BACKGROUND OF THE INVENTION

The ability of numerous bacteria to synthesize and accumulate a polymer of β-hydroxybutyric acid (polyhydroxybutyrate, PHB) as an energy storage compound has long been recognized. The most commonly found compound of this class is poly(D(−)-3-hydroxybutyrate). However, some microbial species accumulate copolymers, which in addition to hydroxybutyrate, may contain longer chain hydroxyalkanoates. These co-polymers are referred to as polyhydroxyalkanoates (PHAs).

Interest has focused on PHAs because these biopolymers are thermoplastics and the physical properties of some PHAS resemble the properties of petro-chemically-based polymers such as polyethylene and polypropylene. However, unlike petro-chemically-based polymers, PHAs are both biocompatible and biodegradable. Certain species of bacteria have the ability to excrete enzymes and degrade PHAs. Because of the prevalence of these bacterial species in many natural environments, PHA is rapidly degraded in the soil and activated sludge. A factor making PHA even more attractive is that microbial PHA production utilizes renewable resources as starting materials, not petroleum. Thus, PHA is of interest as a renewable source of biodegradable thermoplastic.

While PHAs have been of general interest because of their biodegradable nature, their actual use as a plastic material has been hampered by their thermal instability. Industrial production of copolymers of hydroxybutyrate and hydroxyvalerate (PHB/V) from large-scale cultivation of bacteria began in 1982. The PHB/V produced in this way was marketed by ICI plc under the trade name Biopol. PHB/V is a thermoplastic having a high degree of crystallinity and a high melting temperature. As a result, PHB/V becomes unstable and degrades at elevated temperatures near its melting temperature. In addition, PHB/V has mechanical problems such as poor flexibility and poor impact resistance. Due to this thermal instability, and PHB/V's poor mechanical properties, commercial applications of PHB or PHB/V have been extremely limited. If these problems were overcome, PHAs could be utilized for many applications. For example, PHA could be used to make medical materials such as surgical thread or bone setting materials, hygienic articles such as diapers or sanitary articles, agricultural or horticultural materials such as multi films, slow release chemicals, fishery materials such as fishing nets and packaging materials.

Efforts to improve the mechanical qualities of PHAs have focused on altering monomer composition. The physical and mechanical properties of PHAs, such as stiffness, melting temperature, extension to break, and resistance to organic solvents, can change considerably as a function of the monomer composition. For example, melting temperature decreases as the level of monomers with greater than five carbons is increased. Studies of polyhydroxy-alkanoate production in *Ralstonia eutropha* (*Alcaligenes eutrophus*) have shown that when the bacteria are cultivated in a medium with carbohydrates such as glucose or fructose as a carbon source, only PHB is accumulated. However, when both carbohydrate and proprionic acid are provided as carbon sources, the bacteria accumulates copolymers of 3-hydroxyvalerate and 3-hydroxybutyrate (Holmes, P. A., Phys. Technol. 16:32–36 (1985):Holmes, P. A., Wright, L. F. and Collins, S. H. European Patents 0 069 497, January 1983 and 0 052 459, December 1985).

Because the properties of PHAs appear to improve with addition of 3-hydroxyacyl monomers with chain length longer than five carbons, efforts have focused on how to increase incorporation of medium chain heteroalkly units (C6 and above). However, these efforts have been made more difficult because many of the microbial strains which make PHAs make only PHB or only PHAs with short chain monomer units (C3 and C4). For example *R. eutropha*, until recently, was thought to only be capable of incorporating chain lengths up to C5. Anderson et al. "Biosynthesis and composition of bacterial poly(hydroxyalkanoates)", *Int. J Biol. Macromol*, Vol. 12, pp 102–105). One approach to this problem had been to genetically engineer microorganisms which are able to incorporate longer chain lengths. Another approach has been to affect copolymer composition by altering the carbon source utilized by the microorganism.

However, the improvements in the quality of the PHAs have been limited. For example, a copolymer comprising 3-hydroxybutyrate (3HB) and 3-hydroxyvalerate units (3HV) produced in *Ralstonia eutropha* is disclosed in EP 0 440 165 A2. The introduction of the 3HV component into the copolymer lowers the crystallinity and improves the flexibility. However, the copolymer still has problems in that the thermal resistance is not optimal for practical use because the melting temperature is such that extensive decomposition occurs during thermal melt molding. Therefore, this copolymer is not commercially used.

A copolymer has been described which contains small amounts of 3-hydroxycaproate or hexanoate (C6)(2.2%) or 3-hydroxyheptanoate (C7)(1.9%) units in *R. eutropha*. However, no C8 incorporation was reported. Ulmer et al. "The Bacterial Synthesis of Functional Poly β-hydroxyalkanoates", *Polymer Preparation*, Vol. 30, No. 2, pp 402–403 (1989).

Another report utilizing *A. eutrophus*, discloses greater incorporation of C6 (6%) into the PHA copolymer. However, despite the use of C6 to C9 fatty acids as the carbon substrate, no C8 incorporation was reported. Volova et al. "Biosynthesis of Heteropolymeric Polyhydroxyalkanoates by Chemolithoautotrophic Bacteria", *Microbiology*, Vol. 67, No. 4 pp. 420–424 (1998). In addition, these copolymers are not ideal in that the melting temperature is about 180° C., and thermal decomposition would be expected to occur during thermal melt molding. Therefore, this copolymer would not be commercially useful.

To be commercially useful, a thermoplastic copolymer must have certain properties such as flexibility and moldability. At the same time it is desirable that the copolymer be biodegradable and be produced from a renewable source such as PHA which is microbially produced. Thus, there exists a need for a PHA copolymer which incorporates medium length hydroxyalkyl monomers and for a process for making such a PHA.

SUMMARY OF THE INVENTION

The present invention eliminates the above mentioned disadvantages of the prior art and provides commercially useful microbially produced copolymers. Specifically, the copolymers of the present invention have increased flexibility and processing ability, reduced thermal decomposition during molding and excellent moldability. The copolymers of the present invention contain higher levels of monomer units with greater than five carbons than previously obtained using native Ralstonia eutropha and have melting point temperatures of about 30 to 150° C. This value is significantly lower than that of polymers previously described from R. eutropha. The lower melting temperature of the copolymers of the present invention renders them more suitable than the copolymers of the prior art for processing purposes such as thermal molding.

The present invention allows for the use of native or genetically engineered microorganisms to produce copolymers containing medium chain length monomers, thus eliminating the need to use genetically engineered strains for this purpose. Other advantages of the present invention will be apparent from the following description. According to the present invention, a copolymer comprises, as repeating units, (i) 1–10 mol % of 3-hydroxyproprionate units (3HP) having the formula (I):

(ii) 50–98 mol % of 3-hydroxybutyrate units (3HB) having the formula (II):

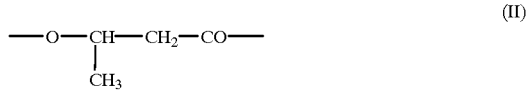

(iii) 1–49 mol % of additional units, wherein the additional units are selected from the group consisting of 3-hydroxyvalerate (HV) having the formula (III), hydroxyhexanoate (HH) having the formula (IV), 3-hydroxy heptanoate (HHp) having the formula (V) and 3-hydroxyoctanoate (3HO) having the formula (VI) and mixtures thereof:

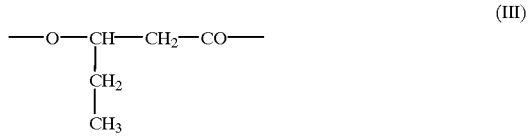

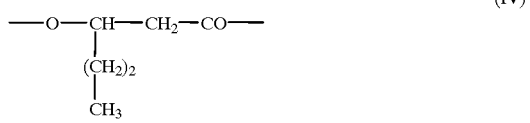

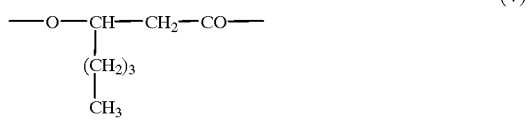

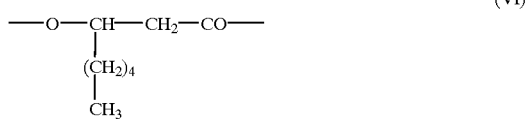

In accordance with the present invention, there is also provided a process for producing the above mentioned copolymer, comprising culturing a microorganism capable of producing a polyhydroxyalkanoate under conditions such that polymer is accumulated, e.g. by limitation of a nutrient, e.g. nitrogen, oxygen or phosphorous source, required for growth but not copolymer accumulation. For at least part of this period of copolymer accumulation, the microorganism is cultured in the presence of fatty acids and/or fatty alcohols with carbon chains containing six or more carbons and a fatty acid oxidation inhibitor to form and accumulate the copolymer within the microorganism cells, followed by recovery of the copolymer.

DETAILED DESCRIPTION OF THE INVENTION

Prior to setting forth the invention, it is helpful to set forth definitions of certain terms to be used hereinafter.

"Short chain" means the fatty acid or alcohol contains five or less carbon atoms.

"Medium chain" means the fatty acid or alcohol contains greater than five carbon atoms.

"Alkyl" means a saturated carbon-containing chain which may be straight or branched, and substituted (mono- or poly-) or unsubstituted.

"PHB" means the homopolymer poly-3-hydroxybutyrate.

"PHA" means a copolymer of hydroxyacyl monomers.

"Native" means that the microorganism has not been genetically engineered to improve or modify the production of PHA by the microorganism.

The present inventors have conducted extensive studies and research toward obtaining a copolymer which could be practically produced on a commercial scale. Desirable characteristics of such a copolymer include excellent moldability, production by native microorganisms, biodegradability and biocompatibility. It was found that by culturing a native microorganism with octanoic acid or the carboxylic acid ester thereof in the presence of a fatty acid oxidation inhibitor, the microorganism produces and accumulates a copolymer which comprises 3HB, 3HP, 3HH, and 3HO units. When the microorganism was cultured with heptanoic acid or the carboxylic acid ester thereof in the presence of a fatty acid oxidation inhibitor, the microorganism produces and accumulates a copolymer which comprises 3HB, 3HP, 3-HV and 3-HHp units. Co-culturing with hepatanoic and octanoic acid results in a copolymer comprising 3HP, 3HB, 3HV, 3HH, 3HHp, and 3HO units. The copolymers obtained have excellent moldability and processing properties. Accordingly, The present invention overcomes the above-mentioned problems of the prior art PHAs.

The present invention will be illustrated in detail as follows:

Microorganism

This invention may be applied to any microorganism capable of producing short chain length polyhydroxyalkanoate. These include, but are not limited to, species belonging to the genus Ralstonia, Zoogloea, Bacillus, Aeromonas, Azotobacter, Clostridum, Nocardia, Halobacterium and Pseudomonas. The microorganism may be native or genetically engineered. Among the above, Ralstonia, Bacillus, Pseudomonas and Azotobacter are typically used. Ralstonia eutropha, formerly referred to as Alcaligenes eutrophus, is most typically used. The bacteriological properties of these microorganisms, belonging to the genus Ralstonia (Alcaligenes) are described in, for example, "BERGEY'S MANUAL OF DETERMINATIVE BACTERIOLOGY, Eighth Edition, The Williams & Wilkins Company/Baltimore".

Cultivation method

The microorganism is cultured according to conventional methods as described in, for example, U.S. Pat. No. 5,364, 778, herein incorporated by reference. Briefly, cultivation of the microorganism preferably comprises a two stage process. In the first stage the microorganism is preferably grown to a certain dry weight per liter, under non-growth limiting conditions on a readily metabolizable substrate, such as a carbohydrate, for example, glucose. In the second stage the substrate is at least in part a fatty acid or fatty alcohol, and at least one nutrient required for growth is limited, such that the growth limiting conditions exist.

Those essential nutrients required for the growth of the microorganism comprise the following elements, which are normally present in readily assimilable form, normally as water soluble salts: nitrogen, phosphorus, sulfur, potassium, sodium, magnesium, calcium, and iron, together with traces of manganese, zinc and copper. While it may be possible to induce copolymer accumulation by restricting the supply of oxygen to the bacterium, it is preferred to restrict the supply of one or more of the essential nutrients. The most practical nutrients to limit are nitrogen, phosphorus or less preferably, magnesium, sulfur or potassium. These microorganisms are cultured according to the conventional two step process.

First step cultivation

For the cultivation in the first step, the conventional cultivation method of growing microorganisms is applicable i.e., to grow the microorganism, a medium and appropriate cultural conditions may be employed.

The culture medium components are not particularly limited, provided that they are substances which can be utilized by the microorganism as carbon sources such as synthetic carbon sources which include methanol, ethanol, and acetic acid; inorganic carbon sources such as carbon dioxide, yeast extract, molasses, peptone, and meat extract, saccharides such as arabinose, glucose, mannose, fructose, galactose, sorbitol, mannitol and inositol. As the nitrogen sources, for example inorganic nitrogen compounds such as ammonia, ammonium salts, nitrates, and/or organic nitrogen containing compounds such as urea, corn steep liquor, casein, peptone, yeast extract, and meat extract may be employed.

The inorganic components can be selected, for example, from calcium salts, magnesium salts, potassium salts, sodium salts, phosphoric acid salts, manganese salts, zinc salts, iron salts, copper salts, molybdenum salts, cobalt salts, nickel salts, chromium salts, boron compounds, and iodine compounds. Also vitamins can be employed.

Generally the culture temperature should be about 20 to 40° C., preferably about 25 to 35° C., and the pH is, for example, about 6 to 10, preferably about 6.5 to 9.5. The cultivation is carried out aerobically under these conditions. The cultivation system may be either batchwise or continuous.

Second step cultivation

The cells obtained in the cultivation by the first step are further cultured under conditions whereby the accumulation of polyhydroxyalkanoate is induced by restricting a critical nutrient, such as nitrogen, phosphorous or oxygen. More, specifically, the microorganism cells are recovered by separation, by a conventional solid-liquid separation means such as filtration or centrifugation, from the culture broth obtained in the first step, and the cells thus obtained are subjected to cultivation in the second step. Alternatively, in the cultivation of the first step, a critical nutrient (such as nitrogen, phosphorus or oxygen) is substantially depleted and the culture broth can be migrated to cultivation in the second step without a recovery by separation of the cells to be cultured therein.

The cultivation in the second step is the same as the cultivation in the first step, except that the amount of one or more of the critical nutrients is restricted in the culture medium or the culture broth, the carbon source comprises one or more fatty acids or fatty alcohols, and a fatty acid oxidation inhibitor is added. The carbon source and the fatty acid oxidation inhibitor may be added at any time during the cultivation in the second step from the initial stage to the end stage of cultivation. Addition at the initial stage is preferable.

Examples of suitable fatty acids or alcohols include but are not limited to: hexanol, heptanol, octanol, nonanol and decanol; hexanoic acid, heptanoic acid, octanoic acid, nonanoic acid, decanoic acid, and longer chain fatty acids; or the salt, ester (including a lactone in the case of a hydroxyl substituted acid), anhydride, amide or halide of the fatty acid; as well as iso and other branched chain fatty acids or alcohols. Preferably medium chain fatty acids are used as the carbon source. More preferably, heptanoic and/or octanoic acid is used as the carbon source. Most preferably, octanoic acid is the carbon source. The carbon source may be used in an amount which can generate a copolymer and does not inhibit the growth of the microorganism, and usually is used in an amount of about 0.1 to 10 g per liter, preferably 1 to 5 g per liter of culture medium or a culture broth. Copolymer variants containing functional groups such as, but not limited to, unsaturated carbon-carbon bonds, hydroxyl, ketone and halide can be made by applying the technology of the present invention and using a modified fatty acid or alcohol substrate.

Examples of suitable fatty acid oxidation inhibitors include but are not limited to: acrylic acid, 2-butynoic acid, 2-octynoic acid, S-phenylproprionic acid, R-phenylproprionic acid, propiolic acid, and trans-cinnamic acid. The inhibitor can be the acid itself or a salt thereof Sodium acrylate is the preferred fatty acid oxidation inhibitor. The fatty acid oxidation inhibitor may be used in an amount which can increase the accumulation of 3HH (C6), 3HHp (C7) and 3HO (C8) copolymers by the desired amount but has an acceptable level of toxicity to the cells. For example sodium acrylate may be used at a concentration in the culture medium of about 1–40 mM, preferably about 10–35 mM and more preferably 25–32 mM.

Extraction of PHA Copolymer for Characterization

From the culture broth thus obtained, the microorganism cells are harvested (recovered by separation) by a conventional solid-liquid separation means such as filtration and centrifugation, and the cells are washed once with 0.1M NaCl, 50 mM TrisHCl 8.0, suspended in water, then freeze dried. PHA copolymer is extracted into chloroform by refluxing for at least about five hours in about 50:1 chloroform to cell dry weight. The extract is filtered through Whatman #4 filter paper, dried down to a minimal volume, and the PHA copolymer is precipitated by adding the viscous solution to 10× volume of diethyl ether/hexane 3/1 v/v. The material is centrifuged in capped Teflon centrifuge tubes and washed once with ethyl ether/hexane before drying under vacuum overnight. Further fractionation of the PHA copolymer is performed by refluxing the solid ethyl ether/hexane precipitated PHA copolymer in boiling acetone for 5 hours. The acetone extract is dried under nitrogen, the PHA copolymer is dissolved into chloroform, and is precipitated with ethyl ether/hexane. Alternatively, the dried cells are directly extracted with acetone and the soluble PHA copolymer is isolated by drying down under nitrogen, dissolving into chloroform, and precipitating with ethyl ether/hexane.

Furthermore, the copolymer product can be recovered from the microorganism using various published and patented procedures to produce PHA copolymer in a variety of useful physical forms. These include chemical extraction using chlorinated solvents (e.g., U.S. Pat. No. 4,562,245), non-chlorinated solvents (WO Publication No. 97/07230), marginal solvents (U.S. Pat. No. 5,821,299), the use of heat and enzymes for isolating PHA particles, an example of which is described in U.S. Pat. No. 4,910,145, or the use of physical means such as air classification (U.S. Pat. No. 5,849,854) and centrifugation (U.S. Pat. No. 5,899,339). These references are incorporated by reference herein.

Analysis of PHA Copolymer

Bacteria from 25 mL cultures are centrifuged, washed once with 0.1M NaCl, 50 mM Tris 8.0, centrifuged, suspended in 2–3 mL of water, frozen and lyophilized for 2 days. The dried cells are reacted in 1 mL chloroform plus 1 mL 15% sulfuric acid in methanol for 4 hours at 100° C. Samples are phase separated with the addition of 1 mL of chloroform plus 1 mL of 1M NaCl. The chloroform phase is treated with anhydrous sodium sulfate to dry, 1 mL is removed and dried in a sample vial under nitrogen or overnight in the hood. Samples are dissolved in 1 mL of acetone plus 1 g/L methyl benzoate and capped. Alternatively, 100 µL of 10 g/L methylbenzoate is added directly to the samples in 1 mL of chloroform and capped. Samples are analyzed on a HP5890 Gas Chromatograph using a 30 m, 0.32 mmID, 0.25 µm film Supelcowax 10 column using helium at a 1 cm$^3$/sec flow rate equal to 20 cm/sec linear flow rate. The injector is set at 225° C. and FID detector at 300° C. The oven temperature is kept at 80° C. for 2 minutes following a 1 µL injection (50:1 split), ramped at 10° C./min to 230° C., and kept at 230° C. for 12 minutes. Alternatively, samples are analyzed on a J&W DB-5MS column (part 122–5531, 30 m, 0.25 mm ID, 0.1 um film) using the same program as above, but the final temperature is kept at 230° C. for 7 minutes. Standard 3-hydroxyalkanoates are purchased from Sigma Aldrich and used to determine the elution times for the various methyl esters. Peaks are further confirmed by subjecting them to mass spectrometry. Gas chromatography is useful for detecting the presence of methyl-3-hydroxybutyrate (C4), methyl-3-hydroxyvalerate(C5), methyl-3-hydroxyhexanoate (C6), methyl-3-hydroxyheptanoate (C7) and methyl-3-hydroxyoctanoate(C8). Proton and $^{13}$C NMR as described in Cao, A., et. al. (1998) Polymer 39(20): 4801–4816, may be used to detect levels of C3, C4 and 3-hydroxyacyl monomers longer than C4.

Separation and mass spectrometric identification of the methyl esters is achieved using a Hewlett-Packard HP5890 Series II gas chromatograph interfaced to a Fisons Trio 2000 quadrupole mass spectrometer (MS). The gas chromatograph (GC) is configured using a J&W Scientific DB-5 ms capillary column (30 meter×0.25 mm I.D., 0.1-µm film thickness) and a split/splitless injection sleeve (Supelco Cat. 2-0486,05). Perfluorotributylamine (PFTBA) is used to calibrate the MS system in EI+ mode. 5% ammonia in methane is used as the CI+ gas. GC/MS selectivity and sensitivity is demonstrated by injecting 1 µL of a 200-µg/mL solution in hexane of C10, C12, C14, C16 alkanes using the following conditions. Two microliters of a 1-mg/mL solution of feedstock material in chloroform is injected using a 40:1 split ratio. The GC oven is held at 60° C. for 3 minutes and then increased 10° C. per minute to 150° C. The mass spectrometer is scanned over a mass range of 40–650 mu using a 1-second scan time and a 0.2-second inter-scan delay. Separate GC/MS runs are performed to collect positive electron ionization (EI+) and positive chemical ionization (CI+) data. EI+ spectral data from each GC peak are electronically searched against an NIST Library to provide possible compound matches. CI+ spectral data is used to provide and/or confirm molecular weight information.

The molecular weight (Mw) and molecular number (Mn) of isolated PHA are determined by size exclusion chromatography. Samples are prepared by dissolution of the polymer in HPLC grade chloroform (0.15–0.2% w/v) and are filtered through 0.2 micron pore size nylon membranes. Analyses are run at room temperature on a Waters system consisting of a 510 pump, a 410 refractive index detector, and a 717 autosampler. Three Waters Ultrastyragel linear columns (one 50×7.8 mm and two 300×7.8 mm) in series are used with chloroform (1 mL/min) as eluent. Calibration is performed with narrow molecular weight polystyrene standards (Polymer Laboratories, EasiCal® part no. 2010-0501). The data are collected and analyzed with Waters Millenium 2020 software (version 2.15.3, with GPC option) which also controlled the Waters system.

To obtain Tg and Tm, Differential Scanning Calorimetry (DSC) measurements are carried out using a Mettler Instrument Corp. (Hightstown N.J.) DSC30. A specific mass of sample is placed in a clean aluminum pan especially made for the DSC30. To obtain the glass transition temperature (Tg), the sample is first heated to about 30° C. above the estimated melting point and is held for three minutes to eradicate any vestiges of crystallinity. The sample is quickly quenched to −80° C. as fast as the apparatus will allow (approximately −80° C./min). The sample is reheated past the melting point at the rate of 10° C. /min. A step-like change in the DSC trace is observed. The midpoint of the step increase is taken as the glass transition. For melting point (Tm) information, the sample is allowed to crystallize for several days. An endothermic peak is observed upon heating. The temperature at the peak is taken as the melting temperature.

Properties of PHA Copolymer

The copolymer thus obtained is a copolymer wherein the hydroxyacyl units form ester bonds with each other. The copolymer of the present invention may be random or block copolymer, preferably random. The ratio of each component can be controlled by changing the kind or concentration of the carbon source and fatty acid oxidation inhibitor. The melting point of the copolymers is most significantly affected by the concentration of medium chain comonomers (C6 and above).

Particularly, the copolymer comprises 50 to 98 mol %, preferably 70 to 96 mol %, more preferably 73–92 mol % of a 3HB component; 1 to 10 mol %, preferably 3 to 10 mol %, more preferably 3 to 7 mol % of a 3HP component; 1 to 49 mol %, preferably 1–20 mol %, more preferably 5–20 mol % of components selected from 3-hydroxyhexanoate, 3-hydroxyheptanoate, 3-hydroxyoctanoate and mixtures thereof.

Preferred polymers have an average molecular weight of about 100,000 to about 2,500,000, particularly about 500,000 to 2,000,000. Preferred polymers also have a glass transition temperature of about −10 to +20° C., more preferably about −5 to +5° C. Furthermore, preferred copolymers have a melting temperature of about 30 to 150° C., preferably about 70 to 130 ° C., and most preferably about 70 to 100 ° C. and therefore, can be molded at a temperature lower than its thermal decomposition temperature of about 150° C.

EXAMPLE 1

A copolymer is prepared by using *Ralstonia eutropha* ATCC 17699.

First Cultivation Step

All incubations are performed at 30° C. in liquid cultures with shaking. A frozen glycerol stock of bacteria is streaked onto solid LB medium (10 g/L Bacto-Tryptone, 5 g/L Yeast Extract, and 10 g/L sodium chloride) plus 1.5% agar. A single colony is selected to inoculate 1 mL of LB broth and then grown for 16 hours. The resulting culture is used to inoculate 25 mL of LB broth, then grown for 8 hours, and used to inoculate 400 mL of LB broth and grown for a further 16 hours. The cells are harvested in a sterile centrifuge bottle and resuspended in 400 mL of Schlegel's medium composed of the following components:

| per liter: | |
| --- | --- |
| Sodium Phosphate dibasic × 12H2O | 9.0 g |
| Potassium Phosphate Monobasic | 1.5 g |
| Ammonium Chloride | 0.1 g |
| Magnesium Sulfate × 7H2O | 0.2 g |
| Calcium Chloride × 2H2O | 0.02 g |
| Fe(III) Ammonium Citrate | 0.0012 g |
| Trace element stock (see below) | 10 ml |

| Trace Element Stock per liter: | |
| --- | --- |
| EDTA | 500 mg |
| Fe Sulfate × 7H2O | 200 mg |
| Zn Sulfate × 7H2O | 10 mg |
| Mn Chloride × 4H2O | 3 mg |
| Boric Acid | 30 mg |
| Co Chloride × 6H2O | 20 mg |
| Cupric Chloride × 2H2O | 1 mg |
| Ni Chloride × 6H2O | 2 mg |
| Sodium Molybdate × 2H2O | 3 mg |

Second Cultivation Step

The cells are portioned out into 25 mL cultures each containing 2 g/L octanoic acid as the carbon source and the cultivation continued at pH 7–8 and 30 to 35° C. Further, various levels of sodium acrylate as the fatty acid oxidation inhibitor are added to individual cultures and the mixtures are incubated for 72 hours.

Separation of Microorganism Cells

Microorganism cells are separated by centrifugal separation from the culture broth obtained and the resultant cells are vacuum dried.

Separation and Recovery of Copolymer

The composition of PHA copolymers are analyzed by Gas Chromatography as described above in the section called "Analysis of PHA Copolymer." Table 1 shows the results that are obtained.

TABLE 1

| Sample | Acrylate | Final OD$_{600}$ | C4*** | C6 | C8 |
| --- | --- | --- | --- | --- | --- |
| Time = 0* | 0 | 6.20 | 6,249 | 0 | 0 |
| 72 h | 0 | 7.65 | 26,426 | 0 | 0 |
| 72 h | 1.3 mM | 7.35 | 24,920 | 0 | 0 |
| 72 h | 2.7 mM | 6.76 | 22,086 | Trace** | 0 |
| 72 h | 4.0 mM | 8.20 | 33,263 | 591 | Trace |
| 72 h | 5.3 mM | 7.37 | 33,315 | 402 | Trace |
| 72 h | 6.6 mM | 7.13 | 31,597 | 550 | Trace |
| 72 h | 8.0 mM | 7.81 | 35,338 | 828 | Trace |
| 72 h | 9.3 mM | 7.70 | 29,080 | 1,849 | Trace |
| 72 h | 10.6 mM | 7.52 | 42,703 | 3,758 | 455 |
| 72 h-No C8 | 0 | 5.64 | 348 | 0 | 0 |

*Sample is analyzed directly from the 400 mL LB broth growth.
**C8 Peak identified by sight, but the area is below the threshold limit.
***C4 = 3-hydroxybutyrate, C6 = 3-hydroxhexanoate, C8 = 3-hydroxyoctanoate This example demonstrates that the inclusion of the medium chain 3-hydroxyalkanoates (C6, C8) into PHA is dependent upon the presence of acrylate, and as the concentration of sodium acrylate is increased, the relative proportion of C6+C8 also increases.

EXAMPLE 2

A copolymer is prepared by using *Ralstonia eutropha* ATCC 17699. Cultures are expanded to 500 mL as described in Example 1 and grown 24 hours in Schlegel's medium containing 2 g/L octanoic acid which is neutralized with sodium hydroxide and 21.3 mM sodium acrylate. The cells are harvested, lyophilized and the PHA extracted into chloroform as described above in "Extraction of PHA for characterization." The PHA is subjected to physical characterization and the results are summarized in Table 2.

EXAMPLE 3

The PHA from Example 2 is fractionated by solubilization in refluxing acetone. The remaining precipitate and the soluble PHA are recovered and analyzed. The results are shown in Table 2.

EXAMPLE 4

PHA is produced in the same way as Example 2, but 10.6 mM sodium acrylate is used and the cultures are incubated at 37° C. The results are shown in One sample is extracted into chloroform, the other is extracted into acetone. The isolated PHA from each is analyzed. The results are shown in Table 2.

TABLE 2

| Example | Acrylate | Extraction[1] | % C3[2] | % C4 | % C6[3] | % C8[3] | $M_n \times 10^{-3}$ | $M_w \times 10^{-3}$ | $T_m$(° C.) | $T_g$(° C.) |
| --- | --- | --- | --- | --- | --- | --- | --- | --- | --- | --- |
| 4 | 10.6 mM | Chl | 1.4 | 95.9 | 2.1 | 0.6 | 798 | 1,860 | 158 | ND |
| 2 | 21.3 mM | Chl | 3.2 | 89.9 | 6.3 | 0.6 | 627 | 1,550 | 119.9, 153.6 | 0.7 |
| 3 | 21.3 mM | Chl → Ace ppt | 3.1 | 91.6 | 4.5 | 0.7 | ND | ND | 163.6 | −1.1 |
| 3 | 21.3 mM | Chl → Ace sol | 3.2 | 87.9 | 7.8 | 1.1 | ND | ND | 128.7 | −2.0 |
| 5 | 29.3 mM | Chl | 5.8 | 84.2 | 8.8 | 1.2 | 662 | 1,550 | 83.8 | −1.9 |
| 5 | 29.3 mM | Ace | 6.5 | 81.7 | 10.2 | 1.6 | 667 | 1,640 | 87.2 | −1.0 |

[1]Chl = extracted with chloroform and ethyl ether/hexane precipitated
Chl → Ace ppt = PHA residue after refluxing the Chl material in acetone
Chl → Ace sol = The soluble portion of the Chl material refluxed in acetone Ace = PHA recovered by refluxing the bacteria overnight in acetone
[2]% calculated from proton NMR
[3]% calculated from total % C6 + % C8 measured by proton NMR, then the relative amounts calculated from gas chromatographic analysis assuming equivalent detector signals per mol of C6 and C8.

EXAMPLE 6

PHA is produced in the same way as Example 1 for the first cultivation step. Following step one, the cells are grown until the level of nitrogen source is depleted and growth is arrested. The culture is fed with medium containing 2 g/L octanoic acid which is neutralized with sodium hydroxide and 29 mM sodium acrylate. The cells are harvested, lyophilized and the PHA extracted into chloroform as described above in "Extraction of PHA for Characterization." A highly moldable copolymer is obtained which has a melting point of 90° C. and a glass transition temperature of −1° C. The copolymer obtained has 15.5 mol % HO, 12.3 mol % HH, 69.2 mol % HB and 3 mol % HP.

EXAMPLE 7

A copolymer is prepared by using *Zoogloea ramigera*. Cultures are grown in the first cultivation step as described in Example 1. Cells are harvested in a sterile centrifuge bottle and resuspended in 400 ml Schlegel's medium containing 10 mM sodium acrylate and 2 g/l heptanoic acid. The cultivation is continued at pH 7–8 and 30° to 35° C. Cells are separated and the PHA recovered as in Example 1. The copolymer obtained has 28 mol % HHp units, 10 mol % HV, 53% HB and 4 mol % HP.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A copolymer comprising, as repeating units, (i) 1–10 mol % of 3-bydroxyproprionate units (3HP) having the formula (I):

—O—CH—CH$_2$—CO—    (I)

(ii) 50–98 mol % of 3-hydroxybutyrate units (3HB) having the formula (II):

(II)

(iii) –48 mol % of additional units, wherein the additional units are selected from the group consisting of 3-hydroxyvalerate (HV) having the formula (III), hydroxyhexanoate (HH) having the formula (IV), 3-hydroxyheptanoate (HHp) having the formula (V) and mixtures thereof:

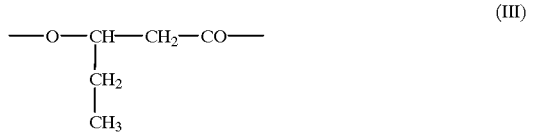

(III)

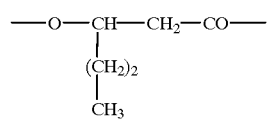

(IV)

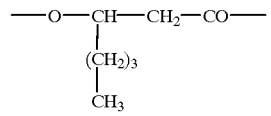

(V)

(iv) 1–49 mol % of 3-hydroxyoctanoate (3HO) having the formula (VI):

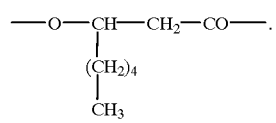

(VI)

2. The copolymer of claim 1 wherein the copolymer has a melting temperature of about 80–100° C. and a glass transition temperature of about −5 to about +5.0° C.

3. The copolymer of claim 1 wherein the copolymer comprises about 11 mol % of units selected from the group consisting of 3-hydroxyhexanoate, 3-hydroxyoctanoate and mixtures thereof and has a melting temperature of about 80–90° C. and a glass transition temperature of about −3 to about +3° C.

4. The copolymer of claim 1, wherein the additional units are selected from the group consisting of 3-hydroxyvalerate, 3-hydroxyheptanoate and mixtures thereof.

5. The copolymer of claim 4 wherein the copolymer comprises (i) 1 to 10 mol % 3HP, (ii) 70–96 mol % 3HB and (iii) 3 to 20 mol % of additional units selected from the group consisting of 3-hydroxyvalerate and 3hydroxyheptanoate and mixtures thereof.

6. The copolymer of claim 1, wherein the additional units are selected from the group consisting of 3-hydroxyhexanoate, 3-hydroxyheptanoate and mixtures thereof.

7. The copolymer of claim 6 wherein the copolymer comprises (i) 1 to 10 mol % 3HP, (ii) 73–94 mol % 3HB and (iii) 5 to 20 mol % of additional units selected from the group consisting of 3-hydroxyhexanoate, 3-hydroxyheptanoate and mixtures thereof.

8. A process for producing a copolymer comprising, as repeating units, (i) 1–10 mol % of 3-hydroxyproprionate units (3HP) having the formula (I):

—O—CH—CH$_2$—CO—    (I)

(ii) 50–98 mol % of 3-hydroxybutyrate units (3HB) having the formula (II):

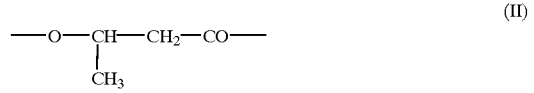

(II)

(iii) 1–49 mol % of additional units, wherein the additional units are selected from the group consisting of 3-hydroxyvalerate (HV) having the formula (II), hydroxyhexanoate (HH) having the formula (IV), 3-hydroxyheptanoate (HHp) having the formula (V)
3-hydroxyoctanoate (3HO) having the formula (VI)
and mixtures thereof:

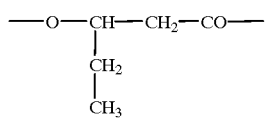
(III)

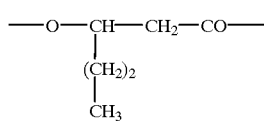
(IV)

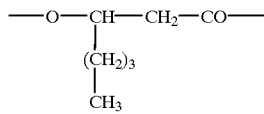
(V)

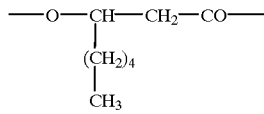
(VI)

said process comprising culturing a microorganism capable of producing a polyhydroxyalkanoate, under at least one restricted condition and in the presence of one or more fatty acid oxidation inhibitor and a carbon source comprising a member selected from the group consisting of medium chain fatty acids, medium chain fatty acid salts, medium chain fatty alcohols, modified fatty acids, modified fatty acid salts, modified fatty alcohols and mixtures thereof.

9. The process of claim 8, wherein the microorganism is native.

10. The process of claim 8, wherein the microorganism is selected from the group consisting of Ralstonia, Zooglea, Bacillus, Aeromonas, Azotobacter, Clostridum, Nocardia, Halobacterium and Pseudomonas.

11. The process of claim 10, wherein the microorganism belongs to the genus Ralstonia.

12. The process of claim 11, wherein the microorganism belongs to the species eutropha.

13. The process according to claim 8 wherein the restricted condition is the nitrogen or the phosphorous source.

14. The process according to claim 8 wherein the carbon source comprises a member selected from the group consisting of octanoic acid, sodium octanoate and octanol.

15. The process according to claim 8 wherein the fatty acid oxidation inhibitor is acrylic acid.

16. The process according to claim 8 wherein the culturing is aerobically effected under the conditions of a temperature from about 20 to about 40° C. and a pH from about 6 to about 10.

17. The process according to claim 8 wherein the copolymer produced comprises 1.0 to 7.0 mol % 3-hydroxypropionate units, 80 to 96 mol % 3-hydroxybutyrate units, and 3.0 to 12 mol % of units selected from the group consisting of 3-hydroxyhexanoate, 3-hydroxyheptanoate and 3-hydroxyoctanoate.

18. A copolymer comprising, as repeating units, (i) 1–10 mol % of 3-hydroxyproprionate units (3HP) having the formula (I):

(I)

(ii) 50–98 mol % of 3-hydroxybutyrate units (3HB) having the formula (II):

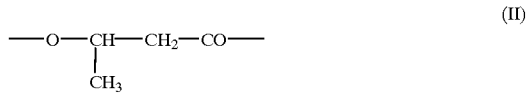
(II)

(iii) 0–48 mol % of additional units, wherein the additional units are selected from the group consisting of 3-hydroxyvalerate (HV) having the formula (III), hydroxyhexanoate (HH) having the formula (IV), 3-hydroxyheptanoate (HHp) having the formula (V) and mixtures thereof:

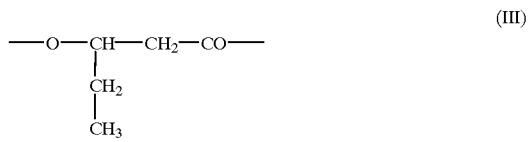
(III)

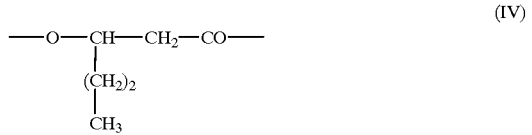
(IV)

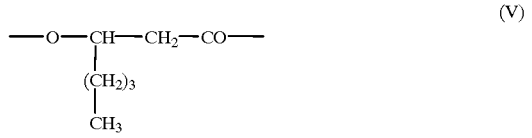
(V)

(iv) 1–49 mol % of 3-hydroxyoctanoate (3HO) having the formula (VI):

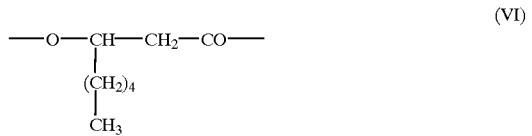
(VI)

wherein the copolymer is made by a process comprising culturing a microorganism capable of producing a polyhydroxyalkanoate under at least one restricted condition and in the presence of one or more fatty acid oxidation inhibitor and a carbon source comprising a member selected from the group consisting of medium chain fatty acids, medium chain fatty acid salts, medium chain fatty alcohols, modified fatty acids, modified fatty acid salts, modified fatty alcohols and mixtures thereof.

* * * * *